United States Patent [19]

Flamholz

[11] Patent Number: 4,679,938
[45] Date of Patent: Jul. 14, 1987

[54] DEFECT DETECTION IN FILMS ON CERAMIC SUBSTRATES

[75] Inventor: Alexander L. Flamholz, Monsey, N.Y.

[73] Assignee: International Business Machines Corporation, Armonk, N.Y.

[21] Appl. No.: 740,158

[22] Filed: Jun. 3, 1985

[51] Int. Cl.$^4$ ............................................. G01N 21/88
[52] U.S. Cl. ................................ 356/237; 250/458.1; 250/459.1
[58] Field of Search ............... 356/237, 239; 250/562, 250/572, 458.1, 459.1

[56] References Cited

U.S. PATENT DOCUMENTS

| | | | |
|---|---|---|---|
| 4,056,716 | 11/1977 | Baxter et al. | 364/515 |
| 4,152,723 | 5/1979 | McMahon et al. | 250/458.1 X |
| 4,221,047 | 9/1980 | Narken et al. | 29/840 |
| 4,245,273 | 1/1981 | Feinberg et al. | 361/382 |
| 4,443,278 | 4/1984 | Zingher | 156/64 |

OTHER PUBLICATIONS

H. D. Kaiser et al., "A Fabrication Technique for Multilayer Ceramic Modules", Solid State Technology/-May 1972, pp. 35-40.
A. J. Blodgett et al., "Thermal Conduction Module: A High—Performance Multilayer Ceramic Package", IBM J. Res. Develop., vol. 26, No. 1, Jan. 1982, pp. 30-36.

Primary Examiner—Davis L. Willis
Assistant Examiner—Matthew W. Koren
Attorney, Agent, or Firm—T. Rao Coca

[57] ABSTRACT

Disclosed is a nondestructive optical method for detecting defects (e.g., open regions) in thin opaque or non-opaque films formed on a ceramic substrate by utilizing the inherent fluoresceability of the ceramic material. The film-clad ceramic is illuminated with an intense optical radiation consisting of at least one wavelength which corresponds to the excitation band(s) of the ceramic component responsible for fluorescence. In case of an opaque film, the incident light will reach the ceramic in regions corresponding to the defects causing these ceramic regions to fluoresce at a different wavelength than that of the incident light. The fluorescent radiation emanating from the ceramic will provide a high contrast optical image of the defects particularly when viewed through a filter which transmits only the fluorescent radiation. In case the film is non-opaque, the incident light will generate fluorescent radiation over the entire substrate—both the defective and non-defective regions. However, the intensity of the fluorescent light emanating from the defective regions will be higher than that from the non-defective regions due to absence of any absorption of the incident and fluorescent light by the defective regions of the film. By analyzing the intensity of the fluorescent light emanating from the entire film-clad substrate, defects in the non-opaque film can be ascertained.

20 Claims, 5 Drawing Figures

DEFECT DETECTION IN FILMS ON CERAMIC SUBSTRATES

BACKGROUND OF THE INVENTION

The invention relates to a method of detecting defects in thin films formed on a ceramic substrate and, more particularly, to a non-destructive method of detecting defects in opaque films such as a conductive metal and non-opaque films such as photoresist, polyimide, and glass.

The trend in electronics today is to achieve ever-increasing component density on a single chip. Increased component density permits greater speed and performance of the circuit while minimizing cost of fabrication.

The desire for increased component density has given rise to very large scale integrated (VLSI) and ultra large scale (ULSI) chips. A VLSI chip typically consists of 4,500–300,000 transistors, equivalent to 1,000–80,000 gates, with 64 input/output (I/O) leads. A ULSI chip consists of a number of transistors and I/O leads exceeding the above limits of VLSI chips coupled with an increase in the logic contained therein.

The design and production of these high density integrated circuits has had a direct effect upon the packaging and interconnection structures that support their insertion into electronic systems. Multilayer ceramic substrates are frequently used to support one or several VLSI chips. An example of a multi-chip module utilizing a multilayer ceramic (hereafter, MLC) substrate is given in U.S. Pat. No. 4,245,273 issued to Feinberg et al. and assigned to the present assignee. Details of fabrication of an MLC substrate is provided in the article entitled "A Fabrication Technique for Multilayer Ceramic Modules" by H.D. Kaiser et al appearing in *Solid State Technology*, May 1972, pp. 35–40. Reference is also made to the article entitled "Thermal Conduction Module: A High Performance Multilayer Ceramic Package", by A.J. Blodgett et al, *IBM J. Res. Develop.*, Vol. 26, No. 1, pp. 30–36, January 1972 wherein is disclosed a 5.5 mm thick and 90-mm square MLC substrate consisting of up to 33 molybdenum metallized alumina layers which are required for power distribution, 350,000 metallized 0.12 mm-diameter vias for layer-to-layer connections and 130 m of x-y wiring to support as many as 118 VLSI chips. The molybdenum metallization is thick, generally in the range of 0.5–10 mils after firing the ceramic.

MLC manufacturers have found that the package performance, specifically, the maximum circuit speed that the MLC substrate will sustain, can be increased by reducing the length of the thick film metal wiring—both the inter-level and x-y wiring—built into the MLC substrate to interconnect the chips. Designers have proposed to reduce interconnection wiring by replacing at least some of the MLC thick film wiring with multilayer thin film wiring. In particular, it has been proposed to use thin film wiring at the MLC chip mounting surface. The thin film wiring is formed at the MLC substrated chip mounting surface as multiple layers of thin metallic film of the order of 30 nm to 3,000 nm separated by a correspondingly thin films of insulator. The multiple thin metal layers are interconnected by vertical metallization which extends through vias that are arranged at predetermined locations. One example of the thin metallic film is a triple layer of chrome-copper-chrome wherein the chrome layers are each about 80 nm thick and the copper layer is about $3\mu$ thick. Examples of the thin film insulator include polyimide and quartz.

Since it is possible to make wiring of smaller dimension (typically about $12\mu$ wide) using thin film technology as compared with thick film technology, it is possible to accommodate more circuits in a substrate plane. Where higher circuit density per plane is achieved, fewer planes are required and, accordingly, the circuit wiring length interconnecting the multiple planes can be reduced. By shortening the interconnection wiring the circuit impedance and any associated parasitic capacitance is lowered thereby increasing the frequency capability of the ceramic package. This technique for increasing frequency capability of the package has been referred to as thin film redistribution (TFR). Details of the TFR technique are provided in U.S. Pat. No. 4,221,047 issued to B. Narken and R. R. Tummala and assigned to the present assignee.

It is anticipated that as ceramic packaging evolves to meet the requirements of ULSI chips, the techniques at present being used for semiconductor integrated circuit (IC) fabrication will be adapted to package fabrication. For example, blanket thin film metal deposition on a ceramic substrate followed by photolithographic and etching techniques to define the blanket layer into a desired metal pattern or deposition of thin films through a suitable mask to form the desired metal pattern will be used to make fine interconnection wiring.

Attendant to the above advanced packaging schemes which provide high interconnection densities is the potential for a reduction in their electrical reliability requiring precise screening of the packages during their fabrication. For example, defects such as thinned-out regions or pin holes formed in the insulator layer may cause an electrical short between two levels of metallization. Another example of defects is imperfections in the thin metallization which leads to electrical shorting between conductors belonging to different levels or adjacent conductors within a given level or electrical opens in these conductors. The reliability problem is particularly a concern since, unlike in the case of semiconductor IC fabrication where the chips are diced from a wafer and defective chips are discarded while salvaging the remainder of the chips diced from the same wafer, the ceramic package, regardless of whether it is a single- or multi-chip package, is individually fabricated. Since the entire ceramic package needs to be utilized for mounting the IC chips(s) thereon, a single defect therein will necessitate scrapping the entire package. Thus, defects in ceramic packages are more likely to be a significant cost factor in the package fabrication.

Added to the above is the unavailability of reliable techniques to detect defects in ceramic packages. The conventional optical defect detection methods employed for ascertaining defects in semiconductor ICs which capitalize on the specular nature of the semiconductor substrate to separate the background signal from the signal corresponding to the defect and provide a sufficient contrast for defect detection are unsuitable in case of ceramic substrates due to the non-specular nature of these substrates. In other words, the ceramic substrate surface, due to its granularity, tends to scatter the incident light rendering the signal corresponding to the defect to be virtually indistinguishable from that corresponding to the background. Consequently, it is not feasible to detect small imperfections in the thin films formed on a ceramic surface.

Reference is made to U.S. Pat. No. 4,056,716 issued to D. W. Baxter et al and assigned to the present assignee which discloses a method of optically inspecting defects in an electrical conductor pattern formed on a ceramic green sheet. This method utilizes the basic step of scanning the green sheet using an optical scanner past a flying-spot scan line and comparing the image detected with the image stored in a storage unit to a master pattern by means of a digital computer. Since this technique relies on reflection of light from the object for inspection thereof, it will not be suitable for inspecting a ceramic surface for the reasons previously discussed herein above.

Another prior art method of detecting defects in thin films on semiconductor substrates by illuminating the substrate with a high intensity light at an oblique angle and observing the reflected light at a preferential angle is also unsuitable for inspecting defects in films on a ceramic substrate since the films conform to the granular surface of the ceramic and scatter light in a manner identical to the ceramic substrate exposed by the defect. As a result, the optical signal arising from the surface of the ceramic exposed by the defect and that from the overlying film will be essentially indistinguishable from each other and the defect in the film will not be identifiable.

The present invention solves these and other problems by a simple, straight-forward optical method for identifying defects in thin films formed on a ceramic substrate by forming a high contrast image of the defects taking advantage of the intrinsic fluorescent property of the ceramic material

SUMMARY OF THE INVENTION

In accordance with the invention, an optical method of detecting defects in thin films formed on a ceramic substrate is provided by which the film is in effect illuminated from its bottom. This enables the light to pass unhindered through the defective (e.g., open) regions therein and be fully/partially absorbed by the non-defective regions thereby creating a bright image of the defective regions in a dark background of the non-defective regions. Illumination of the film from the bottom thereof is accomplished by causing the ceramic substrate to fluoresce at its characteristic wavelength(s) by shining on the substrate optical radiation of a wavelength which excites the fluorescence.

In general, the fluorescent light emanating from the ceramic substrate will be of a different wavelength than that of the incident light and will be partially or fully blocked depending on whether the overlying film is non-opaque (transparent or semi-transparent) or opaque to the fluorescent light. If the film is non-opaque, the intensity of fluorescent light emerging from the substrate region corresponding to the defective regions of the film will be higher that that from the substrate region corresponding to the nondefective regions. If the film is opaque to fluorescent light, then this light will emerge only from the defect regions of the film. Thus, regardless of whether the film is opaque or non-opaque, a high contrast image of the film defects will be obtained.

To enhance the defect detection, a narrow band filter tailored to transmit only the fluorescent wavelength(s) can be used.

BRIEF DESCRIPTION OF THE DRAWINGS

The novel features, process steps and characteristics of the invention are set forth in the appended claims. The invention, itself, however, will be best understood by reference to the detailed description which follows in conjunction with the accompanying drawings, wherein:

DETAILED DESCRIPTION

The present invention is an unique method of detecting defects in a thin film formed on a ceramic substrate. The thin films that can be inspected for defects include those which are opaque and non-opaque to visible or near-visible radiation. An example of an opaque film is a thin metallization layer. An example of a non-opaque film is a dielectric material such as polyimide and quartz and an organic material such as photoresist. It is appreciated that opacity of a material is a function of the wavelength of the radiation. For example, some dielectric materials which are transparent to visible wavelengths are, in fact, opaque to ultraviolet wavelengths. Consequently, if such a dielectric is inspected for defects with ultraviolet radiation it would appear opaque. Defects that can be conveniently detected by the invention include pinholes, pattern disconnections, protrusions, missing intrusions, imperfections such as thinned-out areas, cracks and opaque spots in a transparent or semi-transparent film.

The invention takes advantage of the inherent fluorescent nature of ceramic materials to cause the ceramic substrate material to glow and thereby illuminate the overlying thin film from the bottom thereof. In other words, the ceramic substrate is transformed into a transient light source which illuminates the thin film from its lower surface. Since the intensity of the fluorescent light emerging from the defective sites in the film will be significantly higher than that from the remainder of the film, the nature and location of the defects in the film can be easily ascertained.

Figure 1:
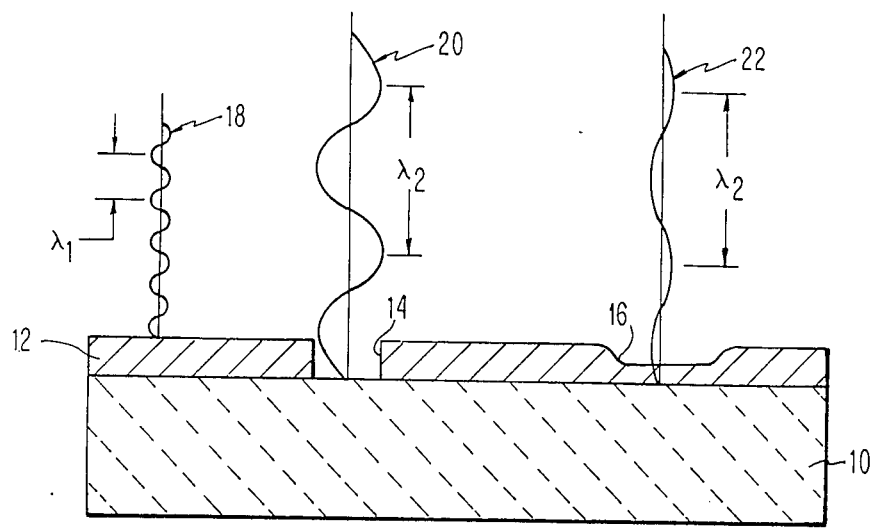
FIG. 1 is a schematic cross-sectional view of a ceramic substrate having a defective thin film thereon showing the typical wavelength relationship between the incident light and the fluorescent light emanating from the ceramic.

To elaborate on the details of the mechanism by which the fluorescent light is generated, reference is made to FIG. 1 where is shown a ceramic substrate 10 having on the top surface thereof a thin film 12. The ceramic material 10 can be any of the typically used materials for packaging IC chips, the fundamental requirement thereof being that it be capable of producing fluorescence. As used herein the term "fluoresceable" refers to the ability to be fluoresced. Thus, "fluoresceable substrate" means a substrate that is capable of exhibiting fluorescence. A specific example of the ceramic material is alumina($Al_2O_3$) which naturally contains impurities such as chromium which generate fluorescent radiation under suitable excitation. Alternatively, the substrate 10 can be of a ceramic material which has been doped with appropriate impurities which would render the material fluorescent or enhance its inherent fluorescing property. The film 12 may be either opaque or non-opaque. For illustrative purposes are shown in film 14 two representative defects 14 and 16. The defect 14 is an open region in the film which may be, for example, a pinhole or a crack. Defect 16 is an imperfection caused by thining out of the film.

To discern the defects 14 and 16 in the thin film 12, the thin film-covered substrate is illuminated with light, designated by numeral 18 in FIG. 1, of a suitable wavelength and intensity which induces fluorescence in the ceramic substrate 10. The intensity and wavelength of the incident light 18 (which has been shown in a waveform representation in FIG. 1) is dictated by the nature (i.e. whether transparent, opaque, etc.) and thickness of of the thin film 12. Typically, the incident light is of a high intensity and short wavelength, that from a mercury lamp. Short wavelength light is preferable since the energy of the photons corresponding to this light is high enough to excite the appropriate fluorescence-generating atoms in the ceramic substrate 10. High intensity light is preferable to make allowance for some absorption of the light in the various materials and the relative inefficiency of the fluorescence mechanism. More importantly, the wavelength of the incident light be such as to match the absorption bands of the ceramic material 10 and induce it to fluoresce. Following excitation of the atoms in the ceramic material by absorption of the incident light 18, these atoms make a transition to their ground state emitting the characteristic fluorescent spectrum which is indicated in FIG. 1, for illustrative purposes, by numerals 20 and 22. Fluorescent light 20 and 22 corresponds to that emerging from the ceramic substrate underlying the defects 14 and 16, respectively. The fluorescent spectrum emitted by the ceramic substrate 10 will typically be confined to a rather narrow wavelength range of less than 10 nm. Consequently, the fluorescent spectrum will appear essentially to be of a single wavelength which can be selectively passed through a filter with little attenuation while simultaneously eliminating the background.

As indicated in FIG. 1, the wavelength of the fluorescent light generated by the ceramic substrate 10 will, in general, be different from that which induced the fluorescence. Typically, the fluorescent wavelength will be longer than the incident wave length. Also, the intensity of the fluorescent light will be different from that of the incident light. This is illustrated in FIG. 1 by the different amplitudes of the incident and emerging light waves.

The optical image corresponding to the defects in the thin film 12 depends upon the nature of the film 12, i.e., whether it is opaque or non-opaque to incident light and to the fluorescent light.

If the thin film 12 is opaque to the incident light, then the incident light will pass only through the open regions 14 in the film 12 and induce fluorescence in only the underlying ceramic material 10 corresponding to the open region 14. Consequently, the fluorescent light will emerge only from the region 14 (and any other areas of the substrate which are not covered by the opaque film 12). Since the fluorescent light will have a different wavelength than the incident light, the image of the defective regions of the film 12 will be readily discernible from that of the non-defective areas of the film. By observing the defect 14 through a narrow band pass filter which transmits only the fluorescent spectrum, a high signal to noise ratio image of the defect is obtained.

If the thin film 12 were non-opaque to the incident light, then the light will pass through the film and will reach the entire substrate surface 10 regardless of whether it corresponds to defective or non-defective region of the film. However, the intensity of the incident light reaching the substrate corresponding to the non-defective region of film 12 will be lower than that reaching the substrate regions corresponding to the defective regions due to absorption by the film. Since the incident light reaches the entire substrate, fluorescent light will be generated by the substrate as a whole. If the film 12 were opaque to the fluorescent light so-generated, then this light will emerge from the open areas 14 in the film while being effectively blocked by the remainder of the film. The resulting image of the defects will be one of a high contrast. If the film 12 were non-opaque to the fluorescent light emerging from the substrate 10, then this light will be transmitted through the film. However, the fluorescent light that is transmitted through the non-defective regions of the film will be of a substantially lower intensity due to inherent absorption of this light by the film. The image of the defects 14 in this situation will still be of a high contrast due to the absorption of both the incident light and fluorescent light emerging from the substrate corresponding to the non-defective areas of film 12 by the film 12 and absence of any such absorption in the defect regions 14 of the film. Likewise, the image of the imperfection 16 in non-opaque film 12 will be of high contrast due to the relative difference in the intensity of the fluorescent light transmitted by the film corresponding to the imperfection 16 and the remainder of the film. As in the previous case, by viewing the defects through a narrow band pass filter which transmits only the fluorescent spectrum, the images of the defects 14 and 16 may be made to stand out.

In addition to the above method of detecting defects in an non-opaque thin film formed on a ceramic substrate by utilizing the intrinsic difference in light absorption by the defective and non-defective regions of the film, defects in non-opaque films can also be ascertained by other methods. One such method is by utilizing a radiation for illuminating the film/ceramic combination which is not only capable of being totally absorbed by the film, but also matches the excitation bands of the ceramic so that this incident radiation will selectively generate fluorescence only in the regions of the ceramic which correspond to defects in the film. In other words, if the film inherently absorbs blue light and the ceramic may be excited to fluoresce using the blue light, then blue light should be used. Another alternative method is by impregnating the non-opaque film with a dye so as to render it opaque for wavelengths corresponding to the excitation radiation.

Figure 2:
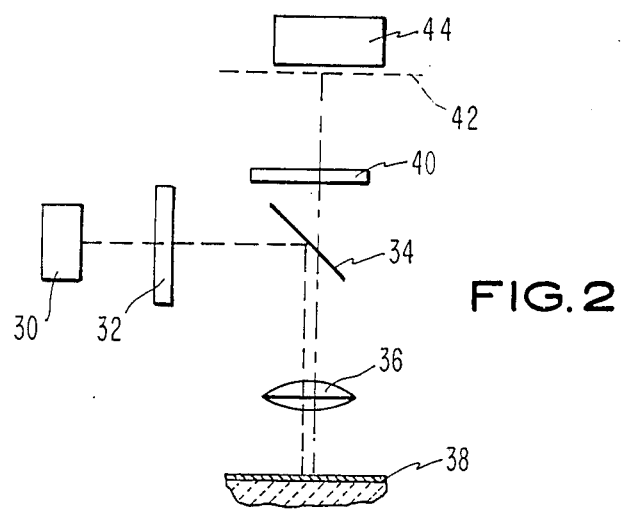
FIG. 2 is schematic illustration of an apparatus for practicing the present invention.

The present invention may be practiced by a fluorescent microscope illustrated in FIG. 2. In this Figure, 30 represents a light source and condenser combination. The light source in 30 is selected to have a sufficiently high intensity in the excitation bands of the ceramic substrate material under inspection. Typical light sources include a mercury xenon or a general purpose xenon source since these have a broad spectral range and can put out a high intensity of light. 32 designates a filter which is necessary if the light source in 30 is a general purpose light source in order to screen out stray light and selectively pass light matching the particular excitation bands of the ceramic material. For example, if the ceramic is alumina having excitation bands at 410 nm and 560 nm, the filter 32 should be one which selectively passes wavelengths in a narrow band centered at 410 nm and 560 nm.

Continuing with reference to FIG. 2, 34 designated a dichroic beam splitter which has a high reflectively in the excitation bands and narrow band transmission in the fluorescent spectrum of the ceramic. The splitter 34 reflects the excitation bands emerging from the filter 32 onto the film-covered ceramic substrate 38. 36 is the imaging objective which in combination with the condenser optics in the source 30 not only illuminates the object 36 under inspection, but also produces an image of the object 38 in the imaging plane 42. The narrow band pass filter 40 transmits the fluorescent spectrum emanating from the object 38, but will block the excitation radiation reflected from the object 38.

In FIG. 2, 44 designates an image detector which could be a simple microscope eyepiece for manual human inspection. Alternatively, the detector 44 can be a sensitive video camera such as silicon intensified target camera. The output from the camera can be displayed on a television monitor for easy inspection of defects in the thin film on the ceramic 38. Additionally, an image processor can be coupled to the detector 44 for high speed automatic detection of defects.

Figure 3:
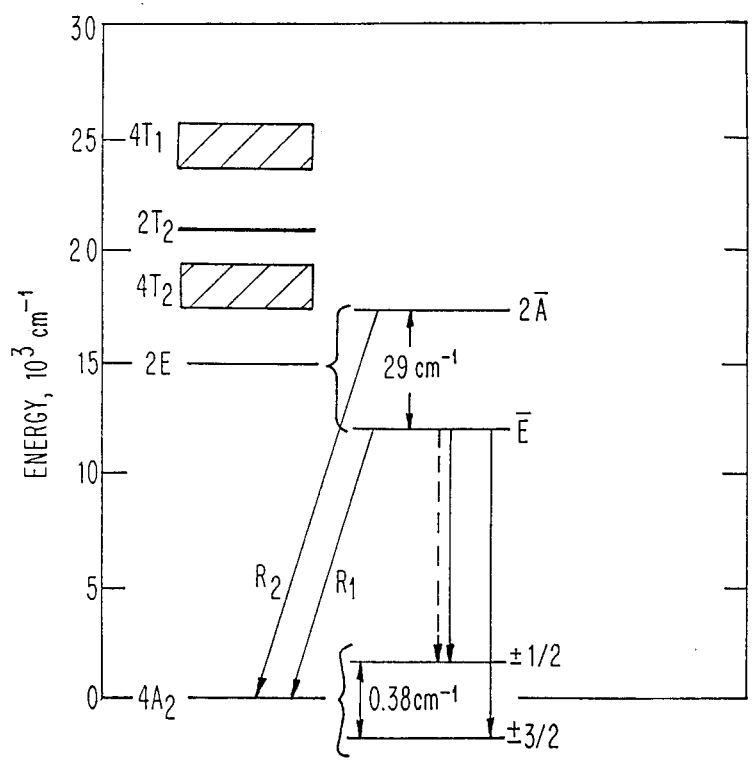
FIG. 3 is the important energy levels of chromium ($Cr^3$) ions in alumina ($Al_2O_3$) substrate and the fluorescent transitions $R_1$ and $R_2$.
Figure 4:
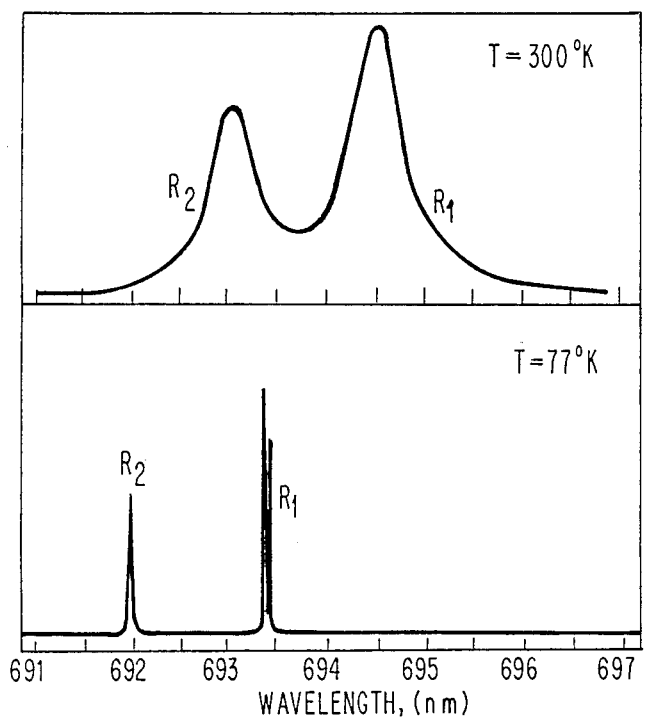
FIG. 4 illustrates the wavelengths corresponding to the fluorescent transitions shown in FIG. 3.

In a specific example of practicing the present invention, an alumina substrate containing chromium ($Cr^3$) impurities is utilized. The alumina is blanket coated with a thin (for example, of thickness about 100 nm) conductive metal in which are present pinholes and cracks of linear dimensions as small as a submicron. Alumina is a naturally fluorescing material. FIG. 3 shows the significant energy levels which give rise to the fluorescent spectrum of alumina which is indicated in FIG. 4. Typical passbands for the filters 32 and 40, beam splitter 34 (Fig. 2) and the alumina excitation are illustrated in FIG. 5.

Referring to FIGS. 2–4, to excite the fluorescence in alumina, it is illuminated with a high intensity light in either or both of the two bands centered at 560 nm and 410 nm (which correspond to $18 \times 10^3$ $cm^{-1}$ and $24.5 \times 10^3$ $cm^{-1}$, respectively, in FIG. 3). As a result, the chromium ions decay into the two 2E levels shown in FIG. 3 from which the fluorescent lines designated by R1 and R1 in FIG. 3 originate. As illustrated in FIG. 4, the fluorescent spectrum of alumina is confined to a narrow wavelength range between 691 nm and 697 nm. Thus, by illuminating alumina with light of wavelength in the range 410–560 nm and viewing the reflected light in a narrow band between about 600–700 nm, defects in thin films on the alumina can be readily gleaned.

Figure 5:
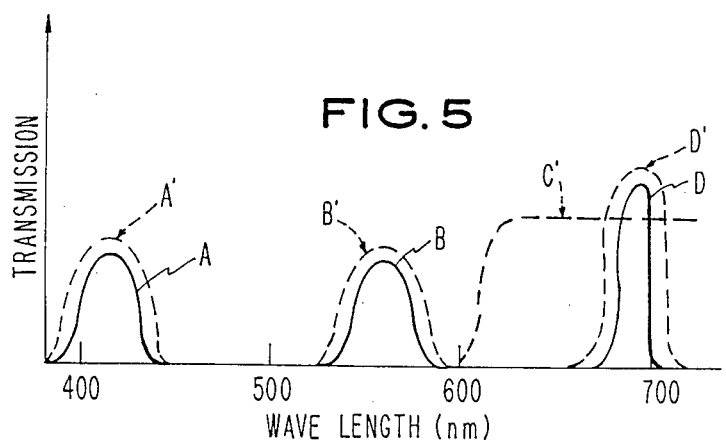
FIG. 5 is a graphical illustration of the typical passbands for the filters, beam splitter and the excitation bands of the alumina material associated with the apparatus of FIG. 2.

The spectral properties of the various fluorescent spectroscopic components for the detection of defects in thin films on alumina should be tailored as indicated in FIG. 5. In this Figure, A and B represent the desired illumination in the excitation bands while A' and B' represent typical single passband or a pair of passbands for the filter 32 in FIG. 2. Filter characteristic C' in FIG. 5 is the low pass filter cutoff for dichroic beam splitter 34 (Fig. 2). D represents the narrow band fluorescence of the substrate and D' is the narrow passband of the filter 40 (FIG. 2).

By using the present invention as described above, defects in thin films formed on ceramic substrates can be detected as bright fluorescent regions in a dark background. The films could be either opaque or non-opaque, the only limitation thereof being that they have either a weak or no fluorescence in the narrow fluorescent spectrum of the ceramic substrate.

While the invention has been described with reference to detection of defects on a single opaque or non-opaque layer of thin film formed directly on a ceramic substrate, it is conducive for detection of defects in multiple layers formed on a ceramic substrate, for example, a metal film (opaque) formed on a polyimide film (non-opaque) which, in turn, overlies a ceramic substrate. The invention can also adapted to detect defects in thin coating formed on any substrate subject only to the requirement that the substrate fluoresce with a significantly higher brightness than the coating in the same spectral band.

While the invention has been particularly described with reference to preferred embodiments thereof, it will be understood by those skilled in the art that various changes in form and detail may be made therein without departing from the spirit and scope of the invention.

I claim:

1. A method of detecting defects in a thin film formed on a fluoresceable substrate comprising;
    illuminating said film with a first radiation;
    generating a second radiation characteristic of the fluorescent spectrum of said substrate; and
    analyzing the intensity of said second radiation to identify localized regions of the substrate where the intensity of said second radiation is higher than that of the remainder of the substrate, whereby said localized regions correspond to said defects.

2. The method as recited in claim 1 wherein said substrate is a ceramic.

3. The method as recited in claim 2, wherein said film is opaque to said first radiation.

4. The method as recited in claim 3, wherein said opaque file is a conductive metal.

5. The method as recited in claim 2, wherein said film is non-opaque to said first radiation.

6. The method as recited in claim 5, wherein said non-opaque film is selected from a group consisting of photosensitive material, polyimide and glass.

7. The method as recited in claim 2, wherein said first radiation comprises at least one wavelength which matches an excitation band of the constituents of the ceramic which generate said fluorescent radiation.

8. The method as recited in claim 7, wherein said first radiation comprises a range of wavelength which are smaller that the wavelengths corresponding to said second radiation.

9. A method for detecting defects in a thin film formed on a ceramic substrate, said method comprising:
    illuminating said film with optical radiation causing said substrate to fluoresce at a wavelength which can pass through said thin film, the wavelength of said fluorescent radiation being different from that of said optical radiation; and
    analyzing the itensity of said fluorescent radiation emanating from said substrate to identify localized regions of the substrate where the intensity of said fluorescent radiation is higher than that from the remainder of the substrate,
    whereby said localized regions correspond to said defects.

10. The method as recited in claim 9, wherein said optical radiation comprises a range of wavelengths.

11. The method as recited in claim 9, wherein said fluorescent radiation comprises a range of wavelengths.

12. The method as recited in claim 11, wherein said wavelengths of said optical radiation are smaller than those of said fluorescent radiation.

13. The method as recited in claim 12, further comprising transmitting said fluorescent radiation through a filter which transmits only said fluorescent radiation prior to said analyzing step.

14. A method for detecting open areas in a thin film formed on a ceramic substrate, said method comprising:
   illuminating said film with optical radiation of a first wavelength range;
   generating a fluorescent radiation of a second wavelength range characteristic of the inherent fluorescent spectrum of said ceramic; and
   analyzing the intensity of said fluorescent radiation emanating from said substrate to identify localized regions of the substrate where the intensity of said fluorescent radiation is higher than that from the remainder of the substrate,
   whereby said localized regions correspond to said open areas.

15. The method as recited in claim 14 further comprising transmitting said fluorescent radiation through a filter which transmits only said fluorescent radiation prior to said analyzing step.

16. The method as recited in claim 15, wherein said film is opaque to said optical radiation.

17. The method as recited in claim 15, wherein said film is non-opaque to said optical radiation.

18. The method as recited in claim 17, wherein said ceramic is alumina.

19. The method as recited in claim 18, wherein the first wavelength range is about 410–560 nm.

20. The method as recited in claim 19, wherein said second wavelength range is about 690–700 nm.

* * * * *